United States Patent [19]

Clark

[11] Patent Number: 5,308,580
[45] Date of Patent: May 3, 1994

[54] SAMPLE COLLECTION AND ANALYTICAL DEVICE

[75] Inventor: Phillip Clark, Stoneham, Mass.

[73] Assignee: Millipore Corporation, Bedford, Mass.

[21] Appl. No.: 885,586

[22] Filed: May 19, 1992

[51] Int. Cl.$^5$ ............................................. G01N 21/00
[52] U.S. Cl. .................................. 422/58; 422/56; 422/61; 422/104; 436/808
[58] Field of Search .................. 422/56–58, 422/61, 104; 436/808

[56] References Cited

U.S. PATENT DOCUMENTS

| | | | |
|---|---|---|---|
| 3,901,657 | 8/1975 | Lightfoot | 422/58 |
| 3,965,888 | 6/1976 | Bender | 422/58 |
| 4,559,949 | 12/1985 | Levine | 422/56 |
| 4,647,430 | 3/1987 | Zweig | 422/58 |
| 4,853,325 | 8/1989 | Vodian et al. | 422/58 |
| 4,963,325 | 10/1990 | Lennon et al. | 422/58 |

Primary Examiner—Lyle A. Alexander
Attorney, Agent, or Firm—Paul J. Cook; Andrew T. Karnakis

[57] ABSTRACT

A sample collection and analysis apparatus is provided comprising a base and a sample collector having a handle and a well. The well contains a porous member having a ligand receptor bound thereto. The base contains an absorbent material for liquids and an opening to expose the absorbent material. The base is provided with means for rendering the sample collector integral with the base and for contacting the porous member with the absorbent material. The apparatus permits detecting or quantitating a target ligand in the sample.

6 Claims, 3 Drawing Sheets

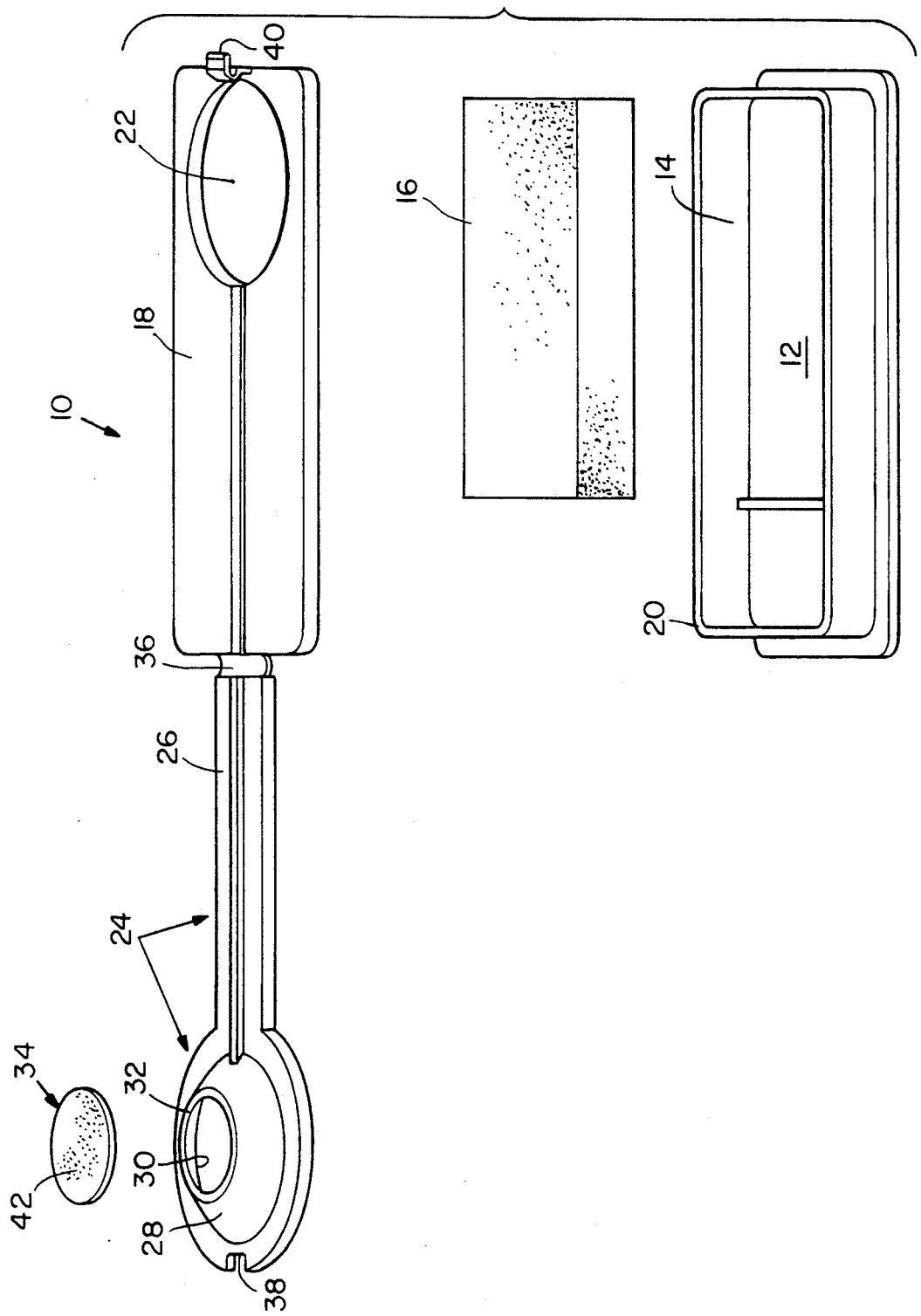

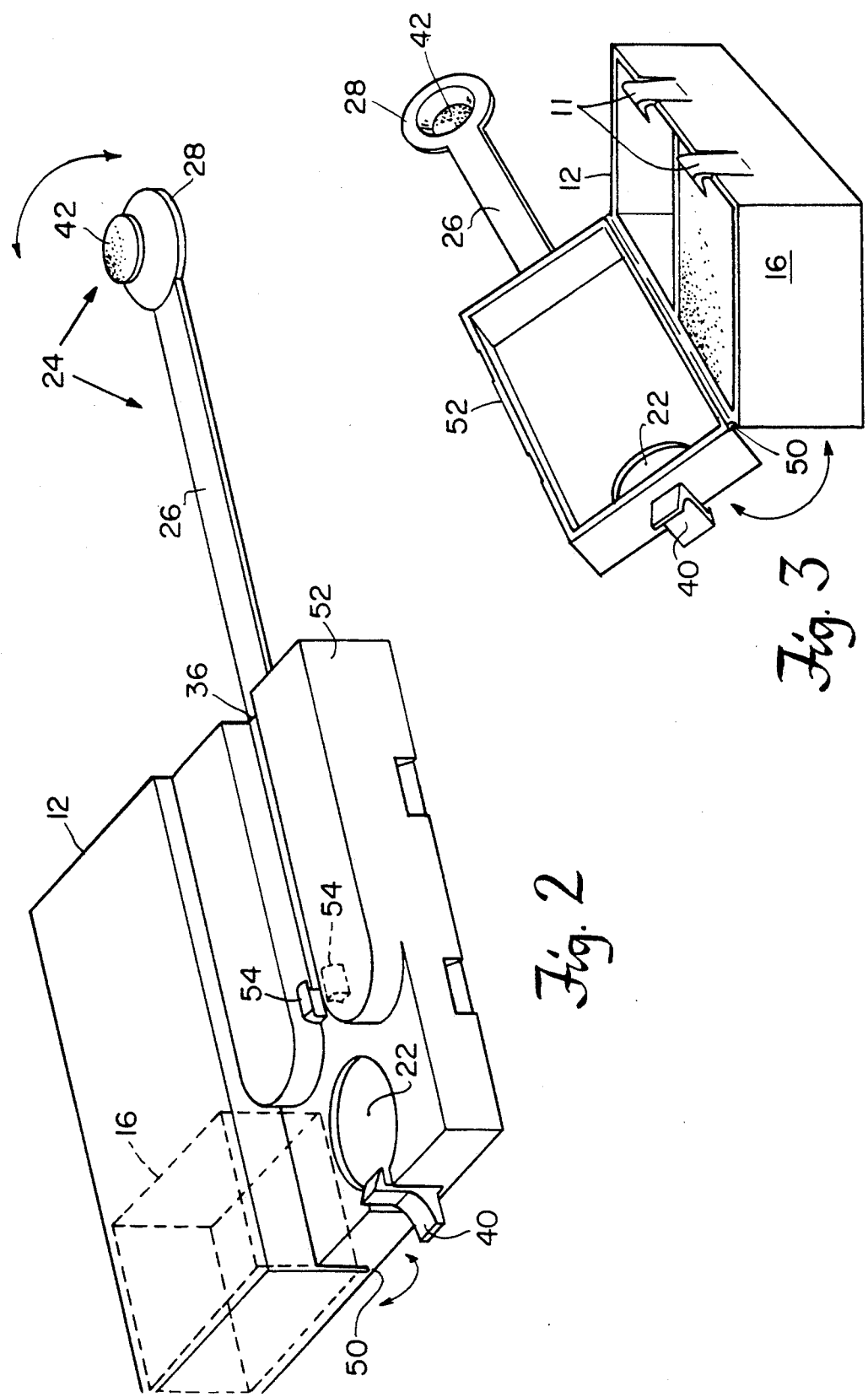

SAMPLE COLLECTION AND ANALYTICAL DEVICE

BACKGROUND OF THE INVENTION

This invention relates to a method and apparatus for collecting and analyzing a sample. More particularly, this invention relates to a method and apparatus having a sample collection means which can be positioned and retained directly on a means for effecting analysis of the sample which can include a sample incubation means.

Prior to the present invention, bioassays such as antigen-antibody reactions, ligand-receptor assays, enzyme-substrate reactions, hybridization nucleic acid reactions, DNA, RNA lectin or the like have been analyzed in apparatus which permits or excludes a sample incubation step. Generally, a receptor is directly bound, by such means as covalently or hydrostatically or indirectly bound, by such means as by being attached to latex particles or magnetic particles and trapped in or on a porous substrate such as a microporous membrane. The sample then is contacted with the membrane so as to effect binding of the ligand to the receptor. The liquid portion of the sample is removed from contact with the membrane and reagents then are introduced in order to determine the presence and/or quantify of the ligand in the sample. Generally, detection of the ligand is determined with a labeled reactant wherein the label can be an enzyme, radionuclide, fluorescent moiety or the like.

It has been proposed in U.S. Pat. No. 4,246,339 to provide a multiwell test device for analyzing a plurality of sample simultaneously. The device includes an upper member having a plurality of wells each having a microporous membrane sealed thereto and having a receptor bound thereon. A bottom member is provided which contains a sorbent material for liquids, a biasing means is interposed between the top and bottom members to bias the membranes away from contact with the sorbent material so that a sample introduced into a well can be incubated in contact with the receptor prior to removing liquid from the wells. Upon completion of incubation, the membranes are contacted with the sorbent material so that filtration of the sample is effected by capillary action. The samples are introduced indirectly into the wells such as with a pipette, or a dropper. This apparatus is not capable of collecting a sample directly such as from a patient or the environment and therefore is undesirable.

U.S. Pat. No. 4,727,019 discloses an apparatus for effecting a ligand receptor assay comprising a top member having a well to which is sealed a microporous membrane. A receptor is bound to the top surface of the membrane. A bottom member is provided which contains a sorbent material for liquids. The top and bottom members are positioned so that the sorbent material always contacts the bottom surface of the membrane. This apparatus is undesirable since it does not permit incubation of the sample in contact with the receptor. This is because the sample introduced into the well immediately is filtered by the membrane due to capillary action by the sorbent material. In addition, the apparatus does not permit collecting a sample directly but requires the use of an intermediary means such as a pipette or dropper. This is undesirable since the sample must be handled a multiplicity of times and may contain dangerous components such as hepatitis virus, human immune virus, (HIV) which can cause acquired immune deficiency syndrome (AIDS).

Accordingly, it would be desirable to provide a method and apparatus which permits sample collection, sample concentration and analysis with a single apparatus. Such a method and apparatus would permit a one step sample collection and analyses with a minimum of sample handling. This, in turn, would improve safety for the sample collection and analysis tasks.

SUMMARY OF THE INVENTION

This invention relates to a method and apparatus for collecting and analyzing a liquid sample. The apparatus includes a collection section and a base section which are formed integrally or which can be rendered integral. The collection section includes a well having two openings and a handle formed integrally with the well. The handle permits the user to be positioned remote from contents in the well and, thus, provides safety to the user. A porous membrane is sealed to one of the well openings and is formed of a material to which a receptor for a target ligand can be bound either directly or indirectly. The receptor is bound to the membrane so that it is exposed to the interior of the well and so that it can come into direct contact with a sample introduced into the well. When the receptor is stable against degradation, it can be introduced on the porous membrane at any time prior to introducing the sample. Alternatively, when the receptor for its target ligand is not stable, it can be introduced onto the top surface of the porous member just prior to introducing the sample so that the receptor is not degraded over time.

The base section includes a hollow volume within which is positioned a sorbent material for liquids. The sorbent material, when contacted with the porous member effects passage of liquid from the well into the sorbent material by capillary action. An opening in the base permits contact of the porous member with the absorbent material in the base. Means are provided on the base for retaining the well of the collection section adjacent the opening of the base. The base also can be provided with means for moving the absorbent material away from contact with the opening or into contact with the opening.

BRIEF DESCRIPTION OF THE DRAWINGS

FIG. 1 is an exploded view of the apparatus of this invention formed integrally.

FIG. 2 is an alternative view of the apparatus of this invention formed integrally.

FIG. 3 is a top view of the apparatus of FIG. 2.

DESCRIPTION OF SPECIFIC EMBODIMENTS

Figure 4:
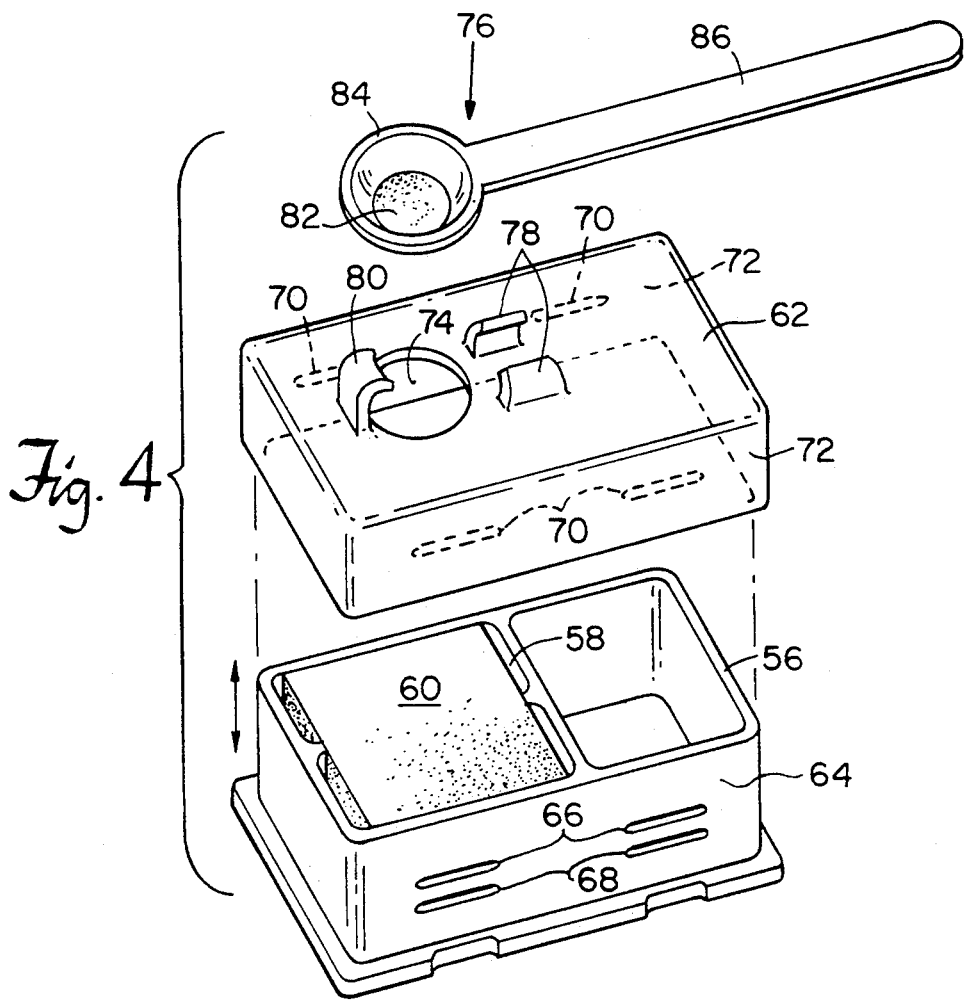
FIG. 4 is an exploded view of an apparatus of this invention formed separately but with means for rendering the apparatus integral.

The collector and analyzer apparatus of this invention comprise a base section and a sample collector section which can be formed integrally or separately and can be rendered integral. The sample collector section includes a well having two openings and a porous member such as a microporous membrane sealed to one opening. The base section includes a hollow volume for retaining an absorbent for liquids as well as an opening in the base. The base on the sample collection section can include means for positioning the absorbent either away from or in contact with the porous member. The porous member is formed of a material which permits a receptor to be bound to it, either directly or indirectly. The base also is provided with means for retaining the sample collector in direct contact with the absorbent material so that when a liquid is introduced into the well, it will pass through the porous member in the well and then into the absorbent material.

The porous member can be a microporous membrane, ultrafiltration membrane, nonwoven filter matrix or the like. The porous member is sealed to an opening in the well so that a top portion of the porous member is exposed to the interior of the well and a bottom surface of the porous membrane is positioned to directly contact the absorbent material on the base. Representative suitable materials for forming the porous member include polyamides, cellulosics, polyvinylidene fluoride, polypropylene, nylon, polyethylene, polycarbonate, nitrocellulose, or the like. The receptor is directly bonded to the porous member such as by covalent bonding or indirectly bonded through a linking moiety such as beads or particles. Suitable receptors are those which have a specific affinity for a target ligand such as an antigen, an antibody, an anti-antibody, a complementary oligmer of DNA or RNA, a substrate for an enzyme, Protein A, avidin-biotin or the like. Examples of such receptors are antibodies to HIV, Antibodies to hepatitus virus, antibodies to toxins, antibodies to pesticides or the like. If the receptor is relatively unstable, it can be applied to the porous member just prior to depositing the sample on the porous member in the well. Otherwise, the receptor can be applied to the porous membrane at any time convenient to the user, or the manufacturer.

Subsequent to binding the receptor to the top surface of the porous member which is exposed within the well, the sample is collected in the well and, if desired, allowed to incubate in contact with the receptor prior to drawing it through the porous member. Flow through the porous member is effected by contacting the bottom surface of the porous member with the absorbent material so that the liquid within the well passes into the absorbent material by capillary action. The target ligand is bound to the receptor on the porous membrane and a second labeled receptor for the bound target ligand such as enzyme-labelled antibody or a biotmylated DNA or oligomer is introduced into the well. The presence or quantification of the target ligand can be determined by measuring directly or indirectly the amount of label bound to the porous member. Unbound labeled second receptor passes through the porous member and into the absorbent material. Suitable absorbent materials include cellulosics, porous polymers, super absorbent gels, or the like.

Referring to FIG. 1, the apparatus of this invention 10 includes a base 12 having a hollow interval volume 14 within which is positioned an absorbent material 16. The top of the base 18 is sealed to surface 20. The top surface 18 is provided with an opening 22 which permits the absorbent material 16 to be exposed. The sample collection section 24 includes a handle 26 and a well 28. The handle has a length to position the user of the apparatus remote from the well contents for reasons of safety. The well has two openings 30 and 32. A porous member 34 through which liquid is drawn is sealed to opening 32. Sample collection section 24 is formed integrally with the top 18 of the base section and is connected thereto by means of hinge 36. In use, the device 10 is grasped by handle 26 and/or base 12 and the opening 30 of the well 28 is contacted with the environment to be sampled such as the mouth of a patient of a body of water in the environment, or an other fluid. The handle 26 permits the sample to be collected remote from the user for improved safety. If desired, the sample can be incubated to permit the receptor and target ligand to bind. The handle 26 is then pivoted about hinge 36 and edge 38 is retained by snap 40 so that the bottom surface 42 of porous member 34 contacts absorbent material 16 exposed within hole 20. The snap 40 can have a two position clasp which permits the porous member 34 to be retained in contact with absorbent material 16 or removed from contact with absorbent material 16.

Referring to FIGS. 2 and 3, the sample collector device includes a base 12 having cover closure snaps 11 and an absorbent material 16 maintained within the base 12. The handle 26 pivots about pivot 36 so that the bottom surface 42 of the porous member can be inserted into hole 22 to contact absorbent 16 and be retained there by means of snap 40. The base 12 can be pivoted about hinge 50 and is retained in contact with top section 52 of the base section by Snaps 11. Snaps 54 serve to further retain the well 28 within opening 22. Base 12 will be closed and snaps 11 are snapped into base 52 prior to effecting the assay. Bases 12 and or 52 hold the absorbent 16. The incubation is achieved by the unsnapping of snap 40 which catches rim of 28. In this portion is flow. The Snaps 54 catch the handle 26 which when released by 40 would flip around because of the memory of the plastic hinge 36.

Referring to FIG. 4, a lower portion 56 of a base is provided with a hollow volume 58 into which is placed an absorbent material for liquids 60. A top portion 62 of the base fits over the outside wall surface 64 of the lower portion 56. The wall surface 64 is provided with two sets of indentations 66 and 68 on opposing surfaces. The indentations 66 and 68 are of a size and shape to accommodate extensions 70 which are positioned on the inside surfaces of wall 72 of top portion 62. The indentations 66 and 68 cooperate with the extensions 70 to effect two different positions of top portion 62 relative to bottom portion 56. When the extensions 70 are fit into the lower indentations 68, the porous member 82 on collection device 76 extends through opening 74 to contact absorbent material 60. When the sample collection device 76 is positioned within brackets 78 and 80, the bottom surface of porous member 82 contacts absorbent material 60 to effect the incubation and filtration processes described above. When extensions 70 are fit into the top set of indentations 66, the porous member 82 is out of contact with the absorbent material 60. When the top portion is in this latter position, the sample collection device can be positioned within brackets 78 and 80 so that the bottom surface of porous member 82 does not contact the absorbent material 60 and incubation can be effected within well 84. The brackets 78 and 80 cooperate with the well 84 and handle 86 so that the sample collection device 76 can be rendered integral with the top portion 62 of the base while the extensions 70 and indentation 66 and 68 permit the top portion 62 and bottom portion 56 to be integral.

Figure 5:
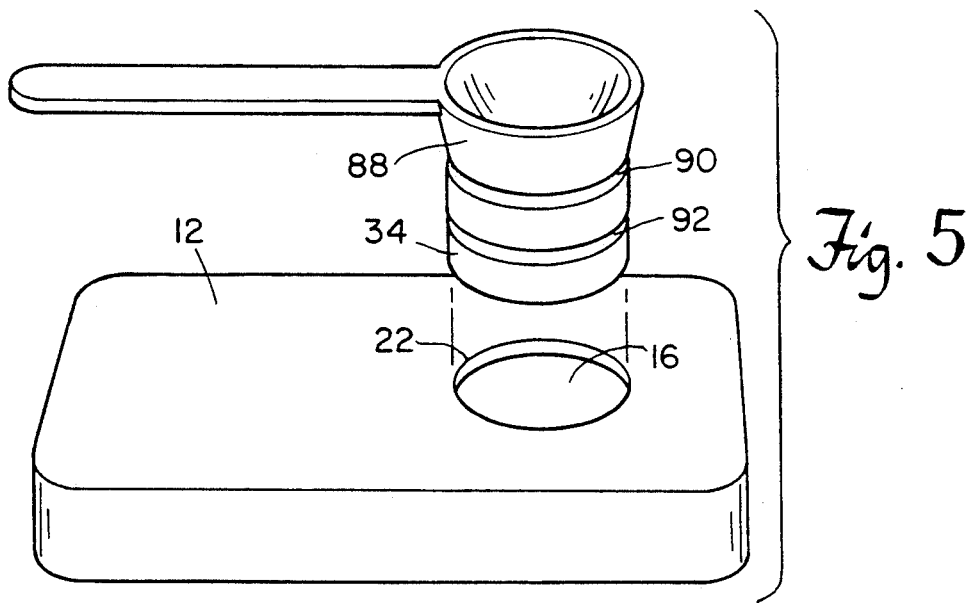
FIG. 5 is an exploded view of an alternative embodiment of this invention with the collection means provided with means for alternately positioning the collection means on the base.

Referring to FIG. 5, the well 88 has an outside surface with a plurality of indentations 90 and 92. The indentation 90 fits with the circumference of opening 22 to contact the porous member 34 at the bottom of well 88 with absorbent material 16. The indentation 92 fits with the circumference of opening 22 to position porous member 34 remote from contact with absorbent material 16 thereby to permit incubation of the contents of well 88.

I claim:

1. A collector apparatus for use in a ligand receptor assay which comprises:

a base having a hollow internal volume, an absorbent for absorbing a liquid housed within said internal volume, an opening in said base to expose said absorbent, a sample collector comprising a handle and a well having two openings, said well having a volume to retain a liquid sample, said well being attached to said handle, a porous member sealed to one of said openings in said well, a receptor capable of binding a target ligand in a liquid sample, bound to a top surface of said porous member, and means on said base and said well to retain said sample collector on said base so that said porous member either (a) is maintained in contact with said absorbent in said base thereby to pass liquid from said sample through said porous membrane to said absorbent by capillary action or (b) is separated from contact with said absorbent thereby to retain said sample within said well and in contact with said receptor.

2. The apparatus of claim 1 wherein said sample collector is formed separately from said base.

3. The apparatus of claim 2 wherein said base is formed from a lower section and an upper section which can be positioned so that said absorbent either (a) is away from contact with said membrane or (b) is in contact with said membrane.

4. The apparatus of claim 1 further comprising means to integrally attach the collector to said base.

5. The apparatus of claim 3 wherein said sample collector is formed separately from said base.

6. The apparatus of claim 3 further comprising means to integrally attach the collector to said base.

* * * * *